United States Patent [19]

Kitamori et al.

[11] Patent Number: 4,557,137
[45] Date of Patent: Dec. 10, 1985

[54] PHOTOACOUSTIC ANALYZER

[75] Inventors: Takehiko Kitamori, Hitachi; Masaaki Fujii, Katsuta; Tsuguo Sawada, Kodaira, all of Japan

[73] Assignee: Hitachi, Ltd., Tokyo, Japan

[21] Appl. No.: 530,061

[22] Filed: Sep. 7, 1983

[30] Foreign Application Priority Data

Sep. 10, 1982 [JP] Japan ................. 57-158547

[51] Int. Cl.⁴ ........................................... G01N 21/00
[52] U.S. Cl. ..................................................... 73/24
[58] Field of Search ................... 73/24; 250/341, 343, 250/351; 356/432, 436, 437

[56] References Cited

U.S. PATENT DOCUMENTS 3,938,365  2/1976  Dewey, Jr. ........................ 73/24
4,200,399  4/1980  Kimble et al. ...................... 73/24

FOREIGN PATENT DOCUMENTS 2089041  6/1982  United Kingdom ................ 73/24

OTHER PUBLICATIONS

T. F. Deutsch, "Optoacoustic Measurements of Energy Absorption in $CO_2$ TEA-Laser-Excited $SF_6$ at 293 and 145 K", Optics Letters, vol. 1, No. 1, pp. 25-27, Jul. 1977.
V. P. Zharov et al., "Optoacoustic Laser Spectroscopy of Excited Vibrational Molecular States", Appl. Physics, pp. 12, 16, 17, 1977.

Primary Examiner—Stephen A. Kreitman
Attorney, Agent, or Firm—Antonelli, Terry & Wands

[57] ABSTRACT

A photoacoustic analyzer comprises an analyzing cell having a beam entrance window and including a cylindrical piezoelectric transducer element forming at least a part of the wall thereof, and a laser beam emitter emitting a laser beam directed toward and into the analyzing cell through the beam entrance window. In the photoacoustic analyzer, the ratio $r/r_o$ between the radius $r$ of the inner side of the analyzing cell and the radius $r_o$ of the incident laser beam is selected to lie within the range of $1 \leq r/r_o \leq 8$.

3 Claims, 4 Drawing Figures

PHOTOACOUSTIC ANALYZER

BACKGROUND OF THE INVENTION

1. FIELD OF THE INVENTION

This invention relates to photoacoustic analyzers, and more particularly to a photoacoustic analyzer suitable for quantitative analysis of fluid with high sensitivity.

2. DESCRIPTION OF THE PRIOR ART

Photoacoustic analyzers for quantitative analysis of fluid have been and are being utilized in the field of, for example, analytical chemistry. However, any theory clarifying the mechanism of generation of a photoacoustic signal in fluid such as a liquid has not yet been established. Therefore, photoacoustic analyzing cells reported already have not been designed to be theoretically optimum.

Especially, the characteristics important for the design of an analyzing cell of a photoacoustic analyzer, such as the intensity distribution of a photoacoustic signal in the analyzing cell and the signal attenuation effect of the analyzing cell have not yet been fully analyzed. Therefore, the prior art photoacoustic analyzer has been defective in that it cannot exhibit its maximum sensitivity determined by the geometrical conditions of the analyzing cell.

SUMMARY OF THE INVENTION

It is a primary object of the present invention to provide a high-sensitivity photoacoustic analyzer for quantitative analysis of fluid, which can efficiently measure a thermoelastic wave induced in the fluid due to incidence of a light beam.

In accordance with the present invention, there is provided a photoacoustic analyzer comprising an analyzing cell having a beam entrance window and including a cylindrical piezoelectric transducer element forming at least a part of the wall thereof, and beam emitting means emitting a light beam directed toward and into the analyzing cell through the beam entrance window, wherein the ratio $r/r_o$ between the radius $r$ of the inner peripheral surface of the analyzing cell and the radius $r_o$ of the incident light beam is selected to lie within the range of $1 \leq r/r_o \leq 8$.

DESCRIPTION OF THE PREFERRED EMBODIMENT

The mechanism of generation of a photoacoustic signal in a liquid was analyzed for determining the optimum conditions for the design of a photoacoustic analyzer suitable for quantitative analysis of the liquid. Herein, the process of theoretical analysis of the mechanism of photoacoustic signal generation in a liquid sample will first be explained briefly, and the manner of optimum design of an analyzing cell in such a photoacoustic analyzer will then be described.

Figure 1:
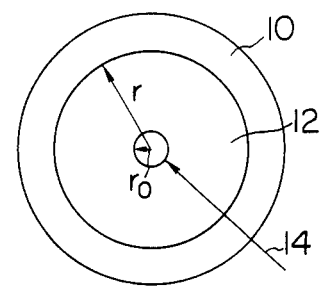
FIG. 1 is a schematic cross-sectional view of a cylindrical piezoelectric transducer element in an analyzing cell of a photoacoustic analyzer used for quantitative analysis of fluid.

FIG. 1 is a schematic cross-sectional view of a cylindrical piezoelectric transducer element 10 in an analyzing cell of a photoacoustic analyzer when used for quantitative analysis of a liquid. A liquid sample 12 is filled in this analyzing cell, and a compressional wave induced in the liquid sample 12 by incidence of a pulse-modulated light beam 14 is detected by the cylindrical piezoelectric transducer element 10. The symbols $r$ and $r_o$ designate the radius of the inner side of the analyzing cell and the radius of the incident light beam spot C respectively. Then, the intensity distribution $I_{(r,t)}$ of the pulse-modulated incident light beam C is expressed by the following equation (1):

$$I_{(r,t)} = I_o e^{-\frac{2S^2 r^2}{r_o^2}} \sum_{n=0}^{[tf]} \delta\left(t - \frac{n}{f}\right) \quad (1)$$

where $I_o$: intensity of light source
S: light scattering factor
t: time
f: light modulation frequency
$\delta(x)$: $\delta(x)$ function
bracket [ ]: Gauss' notation The thermoelastic wave $P_{(r,t)}$ induced by incidence of the light beam C is expressed by the following equation (2):

$$\left(\frac{1}{C^2} \cdot \frac{\partial^2}{\partial t^2} - \nabla^2\right) P_{(r,t)} = \epsilon I_{(r,t)} \quad (2)$$

where $\nabla$ is a differential operator and $\epsilon$ a constant.

Figure 2:
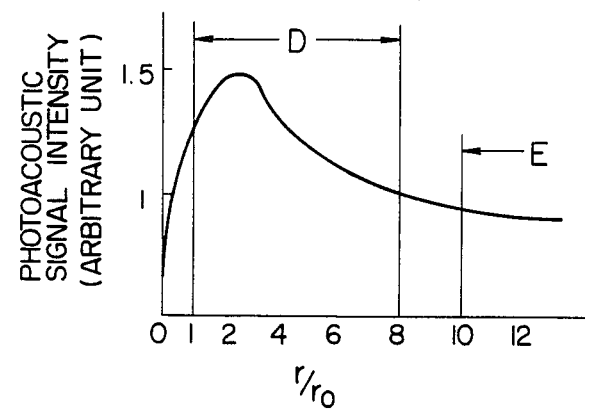
FIG. 2 is a graph showing how a voltage induced in the piezoelectric transducer element varies relative to the ratio $r/r_o$ between the radius $r$ of the inner peripheral surface of the analyzing cell and the radius $r_o$ of the incident light beam.

When the equations (1) and (2) are solved under suitable boundary conditions on the liquid and cell boundary, and the factors including the intensity distribution of the thermoelastic wave in the liquid-sample analyzing cell and the characteristic of the piezoelectric transducer element 10 are taken into account, the dependence of the photoacoustic signal intensity V on the radius $r$ of the inner side of the analyzing cell is found. The relation is shown in the equation (3):

$$V_{(r)} = \eta r^{-1} \cdot r_o e^{-\frac{2S^2 r^2}{r_o^2}} \left\{ I_o^2 \left(\frac{2S^2 r^2}{r_o^2}\right) + \frac{1}{\pi^2} K_o^2 \left(\frac{2S^2 \cdot r^2}{r_o^2}\right) \right\}^{\frac{1}{2}} \quad (3)$$

where n: constant
$I_o(x)$: Modified Bessel function of zeroth-order deformation
$K_o(x)$: Modified Hankel function of zeroth-order deformation FIG. 2 shows the sensitivity characteristic of the analyzing cell calculated according to the equation (3). It can be seen from FIG. 2 that a high voltage is induced when the ratio $r/r_o$ is selected to lie within the range of $1 \leq r/r_o \leq 8$. Actually, the radius r of the inner side of the analyzing cell cannot be made smaller than the radius $r_o$ of the incident light beam spot. It has therefore been found that the ratio $r/r_o$ between the radius r of the inner side of the analyzing cell and the radius $r_o$ of the incident light beam is to be selected to lie within the above range.

Figure 3:
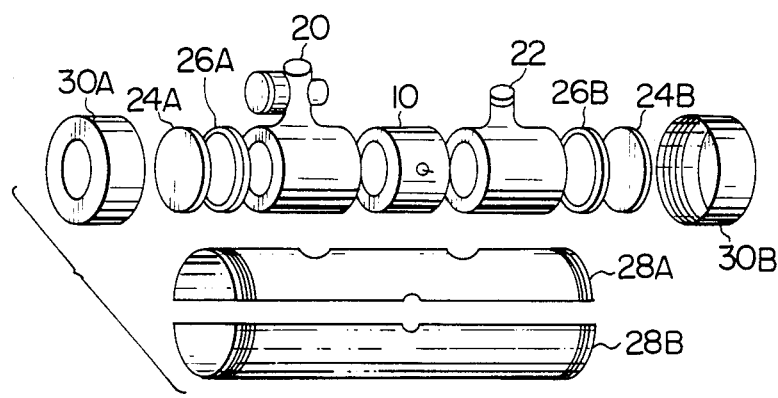
FIG. 3 is an exploded perspective view of a preferred embodiment of the photoacoustic analyzer according to the present invention.
Figure 4:
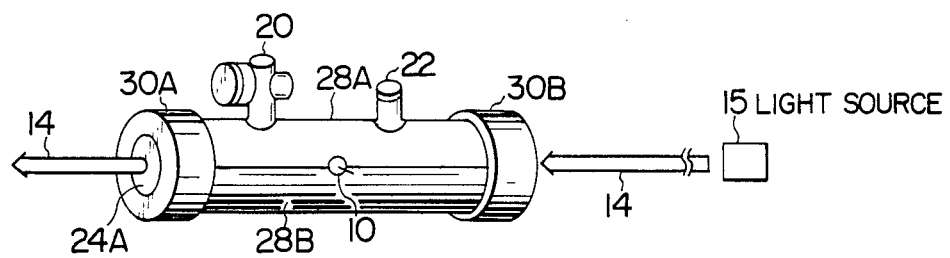
FIG. 4 is a perspective view of the assembly of the parts shown in FIG. 3.

A preferred embodiment of the present invention based on the results of the research and study above described will now be described with reference to FIGS. 3 and 4. The analyzing cell of the photoacoustic analyzer shown in FIGS. 3 and 4 includes a cylindrical piezoelectric transducer element 10 disposed in the middle thereof, and an outlet member 20 and an inlet member 22 for a liquid sample are coupled at respective ends thereof to both ends respectively of the cylindrical piezoelectric transducer element 10. Windows 24A and 24B are provided at the other ends of the liquid-sample outlet and inlet members 20 and 22 respectively. A laser beam 14 emitted from a laser emitter 15 is directed toward and into the analyzing cell, charged with a liquid sample, through the beam entrance window 24B of the analyzing cell and leaves the analyzing cell through the beam exit window 24A. Packings 26A and 26B are interposed between the liquid-sample outlet member 20 and the beam exit window 24A and between the liquid-sample inlet member 22 and the beam entrance window 24B respectively so that the thermoelastic wave generated due to irradiation of the liquid sample with the laser beam 14 may not leak outside the analyzing cell. Further, in order to prevent the analyzing cell from being externally vibrated, the beam exit window 24A, packing 26A, liquid-sample outlet member 20, piezoelectric transducer element 10, liquid-sample inlet member 22, packing 26B and beam entrance window 24B are disposed in the above order in a pair of covers 28A and 28B. Caps 30A and 30B close the both ends of the covers 28A and 28B to combine them into an integral unit.

Suppose that the radius $r_o$ of the incident laser beam 14 is 0.6 mm. Then, the optimum value of the radius r of the inner side of the analyzing cell is between 0.6 mm and 4.8 mm according to the equation (3). In this case, the sensitivity of the analyzing cell is maximum when the radius r of the inner side of the analyzing cell is about 1.2 mm, and this maximum sensitivity is about 1.5 times as high as that of a prior art analyzing cell in which the radius r is about 6 mm.

In FIG. 2, the symbol E represents the range of the ratio $r/r_o$ between the radius r of the inner side of the analyzing cell corresponding to an analyzing cell of a prior art photoacoustic analyzer of this kind and the radius $r_o$ of the incident light beam, and the symbol D represents the range of the ratio $r/r_o$ according to the embodiment of the present invention. It will be seen from FIG. 2 that the value of the ratio $r/r_o$ according to the embodiment of the present invention is smaller than that of the prior art, and, therefore, the sensitivity of the analyzing cell according to the present invention is about 1.1 to 1.5 times as high as that of the prior art analyzing cell.

According to the embodiment of the present invention, the radius r of the inner side of the analyzing cell is considerably smaller than that of the prior art analyzing cell so that the required volume of the liquid sample can be reduced by about 17% to 56%.

The sensitivity of a photoacoustic analyzing cell is proportional to the intensity of an incident light beam. Therefore, the sensitivity of the analyzing cell can be increased by 50% when the intensity of the light source is increased by 50%. However, when, for example, a laser beam emitter is used as the light source, it is more preferable to optimize the radius of the inner side of the analyzing cell as in the case of the embodiment of the present invention than to increase the intensity of the light source, since the size of the laser beam source can be made smaller.

We claim:

1. A photoacoustic analyzer comprising an analyzing cell having a beam entrance window and including a cylindrical piezoelectric transducer element forming at least a part of the wall thereof, and beam emitting means emitting a light beam directed toward and into said analyzing cell through said beam entrance window, wherein the ratio $r/r_o$ between the radius r of the inner side of said analyzing cell and the radius $r_o$ of said incident light beam is selected to lie within the range of $1 \leq r/r_o \leq 8$.

2. A photoacoustic analyzer as claimed in claim 1, wherein said beam emitting means emits a laser beam.

3. A photoacoustic analyzer as claimed in claim 1, wherein for maximum sensitivity of said analyzing cell in which the radius r of the inner side of said analyzing cell is about 1.2 mm, the radius $r_o$ of said incident light beam is selected to be about 0.6 mm.

* * * * *